United States Patent
Ingram et al.

(10) Patent No.: US 10,207,217 B2
(45) Date of Patent: Feb. 19, 2019

(54) REMOVAL OF HYDROGEN SULPHIDE AND CARBON DIOXIDE FROM A STREAM OF FLUID

(71) Applicant: BASF SE, Ludwigshafen (DE)

(72) Inventors: Thomas Ingram, Mannheim (DE); Ralf Notz, Ludwigshafen (DE); Gerald Vorberg, Speyer (DE); Georg Sieder, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 53 days.

(21) Appl. No.: 15/506,635

(22) PCT Filed: Aug. 20, 2015

(86) PCT No.: PCT/EP2015/069154
§ 371 (c)(1),
(2) Date: Feb. 24, 2017

(87) PCT Pub. No.: WO2016/030272
PCT Pub. Date: Mar. 3, 2016

(65) Prior Publication Data
US 2017/0282115 A1    Oct. 5, 2017

(30) Foreign Application Priority Data

Aug. 25, 2014  (EP) .................... 14182101

(51) Int. Cl.
*B01D 53/14* (2006.01)
*B01D 53/52* (2006.01)
(Continued)

(52) U.S. Cl.
CPC ..... *B01D 53/1462* (2013.01); *B01D 53/1493* (2013.01); *C07C 217/08* (2013.01);
(Continued)

(58) Field of Classification Search
None
See application file for complete search history.

(56) References Cited

U.S. PATENT DOCUMENTS

| | | | |
|---|---|---|---|
| 4,471,138 A | 9/1984 | Stogryn | |
| 4,537,753 A | 8/1985 | Wagner et al. | |

(Continued)

FOREIGN PATENT DOCUMENTS

| | | |
|---|---|---|
| CA | 1290553 | 10/1991 |
| CA | 1295810 | 2/1992 |

(Continued)

OTHER PUBLICATIONS

Attari et al., "Sampling and Analysis of Natural Gas Trace Constituents." Institute of Gas Technology (Sep. 1993).*

(Continued)

*Primary Examiner* — Daniel Berns
(74) *Attorney, Agent, or Firm* — Oblon, McClelland, Maier & Neustadt, L.L.P.

(57) ABSTRACT

A process for removing hydrogen sulfide and carbon dioxide from a fluid stream comprises a) an absorption step in which the fluid stream is contacted with an absorbent comprising an aqueous solution (i) of an amine of the general formula (I)

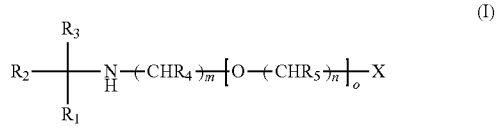

in which $R_1$, $R_2$ and $R_3$ are each independently selected from $C_{1-4}$-alkyl and $C_{1-4}$-hydroxyalkyl; each $R_4$ is independently (Continued)

selected from hydrogen, $C_{1-4}$-alkyl and $C_{1-4}$-hydroxyalkyl; each $R_5$ is independently selected from hydrogen, $C_{1-4}$-alkyl and $C_{1-4}$-hydroxyalkyl; X is OH or $NH(CR_1R_2R_3)$; m is 2, 3, 4 or 5; n is 2, 3, 4 or 5; and o is 0 or 1; and optionally (ii) at least one tertiary amine, where the molar ratio of (i) to (ii) is greater than 0.05; wherein at least 90% of the hydrogen sulfide is removed from the fluid stream and selectivity for hydrogen sulfide over carbon dioxide is not greater than 8, wherein a $CO_2$- and $H_2S$-laden absorbent is obtained; b) a regeneration step in which at least a substream of the $CO_2$- and $H_2S$-laden absorbent is regenerated and a regenerated absorbent is obtained; and c) a recycling step in which at least a substream of the regenerated absorbent is recycled into the absorption step a). The process allows a high level of hydrogen sulfide removal with a simultaneously high coabsorption of carbon dioxide.

16 Claims, 13 Drawing Sheets

(51) Int. Cl.
*B01D 53/78* (2006.01)
*B01D 53/96* (2006.01)
*C07C 217/08* (2006.01)
*C07C 217/28* (2006.01)
*C07C 217/42* (2006.01)

(52) U.S. Cl.
CPC ............ *B01D 2252/2026* (2013.01); *B01D 2252/2041* (2013.01); *B01D 2252/20405* (2013.01); *B01D 2252/20426* (2013.01); *B01D 2252/20431* (2013.01); *B01D 2252/20484* (2013.01); *B01D 2252/502* (2013.01); *B01D 2252/504* (2013.01)

(56) References Cited

U.S. PATENT DOCUMENTS

| | | | |
|---|---|---|---|
| 4,551,158 | A | 11/1985 | Wagner et al. |
| 4,553,984 | A | 11/1985 | Volkamer et al. |
| 4,997,630 | A | 3/1991 | Wagner et al. |
| 4,999,031 | A | 3/1991 | Gerhardt et al. |
| 6,436,174 | B1 | 8/2002 | Grossmann et al. |
| 2008/0019899 | A1 | 1/2008 | Mak et al. |
| 2010/0288125 | A1* | 11/2010 | Vorberg ............ B01D 53/1462 95/181 |
| 2013/0243676 | A1 | 9/2013 | Siskin et al. |

FOREIGN PATENT DOCUMENTS

| | | |
|---|---|---|
| EP | 0 084 943 A2 | 8/1983 |
| EP | 0 121 109 A2 | 10/1984 |
| EP | 0 159 495 A2 | 10/1985 |
| EP | 0 190 434 A2 | 8/1986 |
| EP | 0 202 600 A2 | 11/1986 |
| EP | 0 359 991 A1 | 3/1990 |
| WO | WO 00/00271 A1 | 1/2000 |
| WO | WO 2005/075056 A1 | 8/2005 |

OTHER PUBLICATIONS

International Search Report dated Mar. 21, 2016 in PCT/EP2015/069154.
Jian-Gang Lu et al., "Selective Absorption of $H_2S$ from Gas Mixtures into Aqueous Solutions of Blended Amines of Methyldiethanolamine and 2-tertiarybutylamino-2-ethoxyethanol in a Packed Column", Separation and Purification Technology, vol. 52, No. 2, XP028035520, Dec. 1, 2006, pp. 209-217.

* cited by examiner

REMOVAL OF HYDROGEN SULPHIDE AND CARBON DIOXIDE FROM A STREAM OF FLUID

The present invention relates to a process for removing hydrogen sulfide and carbon dioxide from a fluid stream, which allows improved carbon dioxide removal combined with sufficient hydrogen sulfide selectivity.

The removal of acid gases, for example $CO_2$, $H_2S$, $SO_2$, $CS_2$, HCN, COS or mercaptans, from fluid streams such as natural gas, refinery gas or synthesis gas is important for various reasons. The content of sulfur compounds in natural gas has to be reduced directly at the natural gas source through suitable treatment measures, since the sulfur compounds form acids having corrosive action in the water frequently entrained by the natural gas. For the transport of the natural gas in a pipeline or further processing in a natural gas liquefaction plant (LNG=liquefied natural gas), given limits for the sulfur-containing impurities therefore have to be observed. In addition, numerous sulfur compounds are malodorous and toxic even at low concentrations.

Carbon dioxide has to be removed from natural gas among other substances, because a high concentration of $CO_2$ reduces the calorific value of the gas. Moreover, $CO_2$ in conjunction with moisture, which is frequently entrained in the fluid streams, can lead to corrosion in pipes and valves. If natural gas is liquefied for transport to give LNG (LNG=liquid natural gas), the $CO_2$ has to be substantially removed beforehand. At the temperature of the liquid natural gas (about −162° C.), the $CO_2$ would resublime and damage parts of the plant. On the other hand, too low a concentration of $CO_2$ may likewise be undesirable, for example in the case of feeding into the natural gas grid, since this can result in too high a calorific value of the gas.

Acid gases are removed by using scrubbing operations with aqueous solutions of inorganic or organic bases. When acid gases are dissolved in the absorbent, ions form with the bases. The absorbent can be regenerated by decompression to a lower pressure and/or by stripping, in which case the ionic species react in reverse to form acid gases and/or are stripped out by means of steam. After the regeneration process, the absorbent can be reused.

A process in which all acid gases, especially $CO_2$ and $H_2S$, are very substantially removed is referred to as "total absorption". In particular cases, in contrast, it may be desirable to preferentially absorb $H_2S$ over $CO_2$, for example in order to obtain a calorific value-optimized $CO_2/H_2S$ ratio for a downstream Claus plant. In this case, reference is made to "selective scrubbing". An unfavorable $CO_2/H_2S$ ratio can impair the performance and efficiency of the Claus plant through formation of $COS/CS_2$ and coking of the Claus catalyst or through too low a calorific value.

Highly sterically hindered secondary amines (these referring to amines having a steric parameter (Taft constant) $E_s$ of more than 1.75) such as 2-(2-tert-butylaminoethoxy)ethanol and tertiary amines such as methyldiethanolamine (MDEA) show kinetic selectivity for $H_2S$ over $CO_2$. These amines do not react directly with $CO_2$; instead, $CO_2$ is reacted in a slow reaction with the amine and with water to give bicarbonate—in contrast, $H_2S$ reacts immediately in aqueous amine solutions. These amines are therefore especially suitable for selective removal of $H_2S$ from gas mixtures comprising $CO_2$ and $H_2S$.

The selective removal of hydrogen sulfide is frequently employed in the case of fluid streams having low partial acid gas pressures, for example in tail gas, or in the case of acid gas enrichment (AGE), for example for enrichment of $H_2S$ prior to the Claus process.

For instance, U.S. Pat. No. 4,471,138 showed that highly sterically hindered secondary amines such as 2-(2-tert-butylaminoethoxy)ethanol, even in combination with further amines such as methyldiethanolamine, have a much higher $H_2S$ selectivity than methyldiethanolamine. This effect was confirmed by Lu et al. in Separation and Purification Technology, 2006, 52, 209-217. EP 0 084 943 discloses the use of highly sterically hindered secondary and tertiary alkanolamines in absorption solutions for selective removal of hydrogen sulfide over carbon dioxide from gas streams.

In the case of natural gas treatment for pipeline gas too, selective removal of $H_2S$ over $CO_2$ may be desirable. The absorption step in natural gas treatment is typically effected at high pressures of about 20 to 130 bar (absolute) and partial acid gas pressures of, for example, at least 0.2 bar for $H_2S$ and at least 1 bar for $CO_2$, which are much higher than the partial acid gas pressures in tail gas treatment.

US 2013/0243676 describes a process for absorption of $H_2S$ and $CO_2$ from a gas mixture with an absorbent comprising a highly sterically hindered tertiary etheramine triethylene glycol alcohol or derivatives thereof and a liquid amine.

In many cases, the aim in natural gas treatment is simultaneous removal of $H_2S$ and $CO_2$, wherein given $H_2S$ limits have to be observed but complete removal of $CO_2$ is unnecessary. The specification typical of pipeline gas requires acid gas removal to about 1.5% to 3.5% by volume of $CO_2$ and less than 4 ppmv of $H_2S$. In these cases, maximum $H_2S$ selectivity is undesirable.

It is therefore an object of the invention to specify a process which allows a high level of hydrogen sulfide removal with simultaneously high coabsorption of carbon dioxide. The regeneration energy required is not to be increased significantly compared to $H_2S$-selective absorbents.

The object is achieved by a process for removing hydrogen sulfide and carbon dioxide from a fluid stream, comprising a) an absorption step in which the fluid stream is contacted with an absorbent comprising an aqueous solution of
(i) an amine of the general formula (I)

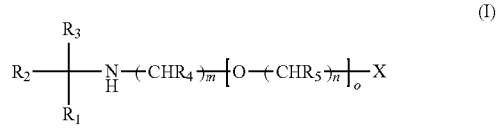

in which $R_1$, $R_2$ and $R_3$ are each independently selected from $C_{1-4}$-alkyl and $C_{1-4}$-hydroxyalkyl; each $R_4$ is independently selected from hydrogen, $C_{1-4}$-alkyl and $C_{1-4}$-hydroxyalkyl; each $R_5$ is independently selected from hydrogen, $C_{1-4}$-alkyl and $C_{1-4}$-hydroxyalkyl; X is OH or $NH(CR_1R_2R_3)$; m is 2, 3, 4 or 5; n is 2, 3, 4 or 5; and o is 0 or 1;
and optionally (ii) at least one tertiary amine, where the molar ratio of (i) to (ii) is greater than 0.05;
wherein at least 90% of the hydrogen sulfide is removed from the fluid stream and selectivity for hydrogen sulfide over carbon dioxide is not greater than 8,
wherein a $CO_2$- and $H_2S$-laden absorbent is obtained;

b) a regeneration step in which at least a substream of the $CO_2$- and $H_2S$-laden absorbent is regenerated and a regenerated absorbent is obtained; and
c) a recycling step in which at least a substream of the regenerated absorbent is recycled into the absorption step a).

According to the prior art, the $H_2S$ selectivity of 2-(2-tert-butylaminoethoxy)ethanol (TBAEE) at low partial $H_2S$ pressures is greater than that of the tertiary amine methyldiethanolamine (MDEA). It has now been found that, surprisingly, the $H_2S$ selectivity of amines of the formula (I) such as TBAEE decreases at high partial acid gas pressures and is less than that of MDEA. This means that amines of the formula (I) under these conditions can absorb $CO_2$ more quickly and hence absorb more $CO_2$ with the same absorber height.

In the absorption step a), the selectivity for hydrogen sulfide over carbon dioxide is not greater than 8, preferably not greater than 6, especially not greater than 5, more preferably not greater than 4. The selectivity is generally greater than 1.

In the present context, "selectivity for hydrogen sulfide" is understood to mean the value of the following quotient:

$$\frac{\frac{y(H_2S)_{feed} - y(H_2S)_{treat}}{y(H_2S)_{feed}}}{\frac{y(CO_2)_{feed} - y(CO_2)_{treat}}{y(CO_2)_{feed}}}$$

in which feed is $y(H_2S)_{feed}$ the molar proportion (mol/mol) of $H_2S$ in the starting fluid, $y(H_2S)_{treat}$ is the molar proportion in the treated fluid, $y(CO_2)_{feed}$ is the molar proportion of $CO_2$ in the starting fluid and $y(CO_2)_{treat}$ is the molar proportion of $CO_2$ in the treated fluid.

Preferably, the cumulated $CO_2$ and $H_2S$ loading of the $CO_2$- and $H_2S$-laden absorbent after the absorption step a) is at least 0.25 mol/mol, more preferably at least 0.30 mol/mol, expressed as the sum total of the molar amounts of $CO_2$ and $H_2S$ dissolved in the absorbent divided by the molar amount of components (i)+(ii).

The absorbent comprises an aqueous solution of an amine of the general formula (I)

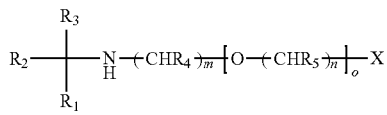
(I)

in which $R_1$, $R_2$ and $R_3$ are each independently selected from $C_{1-4}$-alkyl and $C_{1-4}$-hydroxyalkyl; each $R_4$ is independently selected from hydrogen, $C_{1-4}$-alkyl and $C_{1-4}$-hydroxyalkyl; each $R_5$ is independently selected from hydrogen, $C_{1-4}$-alkyl and $C_{1-4}$-hydroxyalkyl; X is OH or $NH(CR_1R_2R_3)$; m is 2, 3, 4 or 5; n is 2, 3, 4 or 5; and o is 0 or 1. $R_4$ in each repeat unit is independently selected from hydrogen, $C_{1-4}$-alkyl and $C_{1-4}$-hydroxyalkyl. $R_5$ in each repeat unit is independently selected from hydrogen, $C_{1-4}$-alkyl and $C_{1-4}$-hydroxyalkyl. Preferably, $R_1$, $R_2$ and $R_3$ are each methyl. $R_4$ is preferably hydrogen or methyl, especially hydrogen. $R_5$ is preferably hydrogen or methyl, especially hydrogen. Preferably, m is 2, 3 or 4, especially 2 or 3, most preferably 2. Preferably, n is 2, 3 or 4, especially 2 or 3, most preferably 2. Preferably, o is 1.

Suitable amines of the formula (I) are 2-(2-tert-butylaminoethoxy)ethanol (TBAEE), 2-(2-tert-amylaminoethoxy)ethanol, 2-(2-(1-methyl-1-ethylpropylamino)ethoxy)ethanol, 2-(tert-butylamino)ethanol, 2-(tert-butylamino)propanol, 2-(tert-butylamino)butanol, (2-(tert-butylamino)ethyl)methylamine and mixtures thereof. In a preferred embodiment, the amine (i) is 2-(2-tert-butylaminoethoxy)ethanol.

The exothermicity of the reaction of amines of the formula (I) with carbon dioxide is greater than the tertiary amines. When an absorbent comprising an amine of the general formula (I) as the sole basic component is used—especially at a low absorbent/fluid stream ratio—the exothermicity can become too high and a desired $H_2S$ specification cannot be achieved under some circumstances. The invention therefore envisages that the absorbent may comprise not only an amine (i) but optionally also at least one tertiary amine (ii). As well as the control of the exothermicity, it has been found that the addition of a tertiary amine (ii) to the amine (i) can control the $H_2S$ selectivity. The higher the proportion of amine (i), the lower the $H_2S$ selectivity, i.e. more $CO_2$ can be removed with the same absorber height. At the same time, the process allows a high level of removal for $H_2S$.

A "tertiary amine" is understood to mean compounds having at least one tertiary amino group. The tertiary amine (ii) preferably comprises exclusively tertiary amino groups, meaning that it does not comprise any primary or secondary amino groups alongside at least one tertiary amino group. The tertiary amine (ii) preferably does not have any acidic groups such as, in particular, phosphonic acid, sulfonic acid and/or carboxylic acid groups.

The suitable tertiary amines (ii) especially include:
1. Tertiary alkanolamines such as
   bis(2-hydroxyethyl)methylamine (methyldiethanolamine, MDEA), tris(2-hydroxyethyl)amine (triethanolamine, TEA), tributanolamine, 2-diethylaminoethanol (diethylethanolamine, DEEA), 2-dimethylaminoethanol (dimethylethanolamine, DMEA), 3-dimethylamino-1-propanol (N,N-dimethylpropanolamine), 3-diethylamino-1-propanol, 2-diisopropylaminoethanol (DIEA), N,N-bis(2-hydroxypropyl)methylamine (methyldiisopropanolamine, MDIPA);
2. Tertiary amino ethers such as
   3-methoxypropyldimethylamine;
3. Tertiary polyamines, for example bis-tertiary diamines such as
   N,N,N',N'-tetramethylethylenediamine, N,N-diethyl-N',N'-dimethylethylenediamine, N,N,N',N'-tetraethylethylenediamine, N,N,N',N'-tetramethyl-1,3-propanediamine (TMPDA), N,N,N',N'-tetraethyl-1,3-propanediamine (TEPDA), N,N,N',N'-tetramethyl-1,6-hexanediamine, N,N-dimethyl-N',N'-diethylethylenediamine (DM-DEEDA), 1-dimethylamino-2-dimethylaminoethoxyethane (bis[2-(dimethylamino)ethyl] ether), 1,4-diazabicyclo[2.2.2]octane (TEDA), tetramethyl-1,6-hexanediamine;
and mixtures thereof.

Tertiary alkanolamines, i.e. amines having at least one hydroxyalkyl group bonded to the nitrogen atom, are generally preferred. Particular preference is given to methyldiethanolamine (MDEA).

The molar ratio of (i) to (ii) is greater than 0.05 and is preferably in the range from 0.1 to 0.9. By varying the molar ratio of (i) to (ii), the $H_2S$ selectivity can be adjusted to the particular requirements within the inventive limits. In spite of reduced $H_2S$ selectivity, the regeneration energy is the same as or less than that of an $H_2S$-selective absorbent.

In general, the total concentration of (i) and (ii) in the aqueous solution is 10% to 60% by weight, preferably 20% to 50% by weight, more preferably 30% to 50% by weight.

In one embodiment, the aqueous solution comprises at least one organic solvent. The organic solvent is preferably selected from sulfolane, glycols such as ethylene glycol, diethylene glycol, ethylene glycol dimethyl ether, triethylene glycol, triethylene glycol dimethyl ether, di- or mono ($C_{1-4}$-alkyl ether) monoethylene glycols and di- or mono ($C_{1-4}$-alkyl ether) polyethylene glycols, N-methylpyrrolidone, N-methyl-3-morpholine, N-formylmorpholine, N-acetylmorpholine, N,N-dimethylformamide, N,N-dimethylimidazolidin-2-one, N-methylimidazole and mixtures thereof.

Preferably, the absorbent does not comprise any sterically unhindered primary or secondary amines. Compounds of this kind act as strong promoters of $CO_2$ absorption. As a result, the $H_2S$ selectivity of the absorbent can be lost.

A sterically unhindered primary or secondary amine is understood to mean compounds having primary or secondary amino groups to which only hydrogen atoms or primary carbon atoms are bonded.

The absorbent may also comprise additives such as corrosion inhibitors, enzymes, etc. In general, the amount of such additives is in the range from about 0.01% to 3% by weight of the absorbent.

The process according to the invention is suitable for treatment of all kinds of fluids. Fluids are firstly gases such as natural gas, synthesis gas, coke oven gas, cracking gas, coal gasification gas, cycle gas, landfill gases and combustion gases, and secondly fluids that are essentially immiscible with the absorbent, such as LPG (liquefied petroleum gas) or NGL (natural gas liquids). The process according to the invention is particularly suitable for treatment of hydrocarbonaceous fluid streams. The hydrocarbons present are, for example, aliphatic hydrocarbons such as $C_1$-$C_4$ hydrocarbons such as methane, unsaturated hydrocarbons such as ethylene or propylene, or aromatic hydrocarbons such as benzene, toluene or xylene.

The absorbent or process according to the invention is suitable for removal of $CO_2$ and $H_2S$. As well as carbon dioxide and hydrogen sulfide, it is possible for other acidic gases to be present in the fluid stream, such as COS and mercaptans. In addition, it is also possible to remove $SO_3$, $SO_2$, $CS_2$ and HCN.

In preferred embodiments, the fluid stream is a fluid stream comprising hydrocarbons, especially a natural gas stream. More preferably, the fluid stream comprises more than 1.0% by volume of hydrocarbons, even more preferably more than 5.0% by volume of hydrocarbons, most preferably more than 15% by volume of hydrocarbons.

The partial hydrogen sulfide pressure in the fluid stream is typically at least 2.5 mbar. In a preferred embodiment, there is a partial hydrogen sulfide pressure of at least 0.1 bar, especially at least 0.5 bar, most preferably at least 1 bar. In a further preferred embodiment, there is a partial carbon dioxide pressure of at least 0.2 bar, especially at least 0.5 bar, most preferably at least 1 bar, in the fluid stream. More preferably, there is a partial hydrogen sulfide pressure of at least 0.1 bar and a partial carbon dioxide pressure of at least 1 bar in the fluid stream. Most preferably, there is a partial hydrogen sulfide pressure of at least 0.5 bar and a partial carbon dioxide pressure of at least 1 bar in the fluid stream. The partial pressures stated are based on the fluid stream on first contact with the absorbent in the absorption step.

In preferred embodiments, a total pressure of at least 3.0 bar, more preferably at least 5.0 bar, even more preferably at least 20 bar, is present in the fluid stream. In general, a total pressure of at most 180 bar, usually at most 120 bar, is present in the fluid stream. The total pressure of the fluid stream corresponds essentially to the pressure in the absorber in the absorption step a).

The absorption step a) is not a total absorption, meaning that the treated fluid stream comprises a reduced concentration of $CO_2$ compared to the concentration in the fluid stream to be treated. The treated fluid stream typically still comprises at least 1.0% by volume of $CO_2$, preferably at least 1.5% by volume of $CO_2$, more preferably at least 2.0% by volume of $CO_2$.

The process according to the invention makes use of a selective removal of hydrogen sulfide over $CO_2$, but the selectivity for hydrogen sulfide over carbon dioxide is not greater than 8. At least 90% of the hydrogen sulfide is removed from the fluid stream. The percentage removal of hydrogen sulfide can be ascertained by conducting a mass balance of the volume flow rate of the fluid stream to be treated (in $m^3$ (STP)) multiplied by the $H_2S$ concentration in the fluid stream to be treated (in % by volume) against the volume flow rate of the fluid stream to be treated multiplied by the $H_2S$ concentration in the fluid stream to be treated.

The person skilled in the art can achieve a high level of hydrogen sulfide removal with a defined selectivity by varying the conditions in the absorption step, such as, more particularly, the absorbent/fluid stream ratio, the column height of the absorber, the type of contact-promoting internals in the absorber, such as random packings, trays or structured packings, and/or the residual loading of the regenerated absorbent.

A low absorbent/fluid stream ratio leads to an elevated selectivity of the absorbent; a higher absorbent/fluid stream ratio leads to a less selective absorption. Since $CO_2$ is absorbed more slowly than $H_2S$, more $CO_2$ is absorbed in a longer residence time than in a shorter residence time. A higher column therefore brings about a less selective absorption. Trays or structured packings with relatively high liquid holdup likewise lead to a less selective absorption. The heating energy introduced in the regeneration can be used to adjust the residual loading of the regenerated absorbent. A lower residual loading of the regenerated absorbent leads to improved absorption.

In the process according to the invention, the fluid stream is contacted with the absorbent in an absorption step in an absorber, as a result of which carbon dioxide and hydrogen sulfide are at least partly scrubbed out. This gives a $CO_2$- and $H_2S$-depleted fluid stream and a $CO_2$- and $H_2S$-laden absorbent.

The absorber used is a scrubbing apparatus used in customary gas scrubbing processes. Suitable scrubbing apparatuses are, for example, columns having random packings, having structured packings and having trays, membrane contactors, radial flow scrubbers, jet scrubbers, Venturi scrubbers and rotary spray scrubbers, preferably columns having structured packing, having random packings and having trays, more preferably columns having trays and having random packings. The fluid stream is preferably treated with the absorbent in a column in countercurrent. The fluid is generally fed into the lower region and the absorbent into the upper region of the column. Installed in tray columns are sieve trays, bubble-cap trays or valve trays, over which the liquid flows. Columns having random packings can be filled with different shaped bodies. Heat and mass transfer are improved by the increase in the surface area caused by the shaped bodies, which are usually about 25 to 80 mm in size. Known examples are the Raschig ring (a hollow cylinder), Pall ring, Hiflow ring, Intalox saddle and the like. The random packings can be introduced into the column in an ordered manner, or else randomly (as a bed). Possible materials include glass, ceramic, metal and plastics. Structured packings are a further development of ordered random packings. They have a regular structure. As a result, it is possible in the case of structured packings to reduce pressure drops in the gas flow. There are various designs of structured packings, for example woven packings or sheet metal packings. Materials used may be metal, plastic, glass and ceramic.

The temperature of the absorbent in the absorption step is generally about 30 to 100° C., and when a column is used is, for example, 30 to 70° C. at the top of the column and 50 to 100° C. at the bottom of the column.

The process according to the invention may comprise one or more, especially two, successive absorption steps. The absorption can be conducted in a plurality of successive component steps, in which case the crude gas comprising the acidic gas constituents is contacted with a substream of the absorbent in each of the component steps. The absorbent with which the crude gas is contacted may already be partly laden with acidic gases, meaning that it may, for example, be an absorbent which has been recycled from a downstream absorption step into the first absorption step, or be partly regenerated absorbent. With regard to the performance of the two-stage absorption, reference is made to publications EP 0 159 495, EP 0 190 434, EP 0 359 991 and WO 00100271.

The process comprises a regeneration step in which the $CO_2$- and $H_2S$-laden absorbent is regenerated. In the regeneration step b), $CO_2$ and $H_2S$ and optionally further acidic gas constituents are released from the $CO_2$- and $H_2S$-laden absorbent to obtain a regenerated absorbent. In general, the regeneration step b) comprises at least one of the measures of heating, decompressing and stripping with an inert fluid.

The $CO_2$- and $H_2S$-laden absorbent is preferably regenerated to a hydrogen sulfide loading corresponding to an equilibrium loading for a hydrogen sulfide content of preferably less than 90%, more preferably less than 50%, of the hydrogen sulfide content of the treated fluid stream. "Equilibrium loading" is understood to mean the hydrogen sulfide content in the absorbent which, under the pressure and temperature conditions at the top of the absorber, is in equilibrium with the specified content of hydrogen sulfide in the treated gas stream that leaves the absorber.

Preferably, the cumulated $CO_2$ and $H_2S$ loading of the regenerated absorbent is less than 0.20 mol/mol, especially less than 0.15 mol/mol. The loading is expressed as the molar amount of $CO_2+H_2S$ dissolved in the absorbent divided by the molar amount of components (i)+(ii).

The regeneration step b) preferably comprises heating of the absorbent laden with the acidic gas constituents. The absorbed acid gases are stripped out by means of the steam obtained by heating the solution. Rather than steam, it is also possible to use an inert fluid such as nitrogen. The absolute pressure in the desorber is normally 0.1 to 3.5 bar, preferably 1.0 to 2.5 bar. The temperature is normally 50° C. to 170° C., preferably 80° C. to 130° C., the temperature of course being dependent on the pressure.

The regeneration step b) may alternatively or additionally comprise a decompression. This includes at least one decompression of the laden absorbent from a higher pressure as exists in the conduction of the absorption step to a lower pressure. The decompression can be accomplished, for example, by means of a throttle valve and/or a decompression turbine. Regeneration with a decompression stage is described, for example, in publications U.S. Pat. Nos. 4,537,753 and 4,553,984.

The acidic gas constituents can be released in the regeneration step b), for example, in a decompression column, for example a flash vessel installed vertically or horizontally, or a countercurrent column with internals.

The regeneration column may likewise be a column having random packings, having structured packings or having trays. The regeneration column has a heater at the bottom, for example a boiler, natural circulation evaporator, forced circulation evaporator or forced circulation flash evaporator. At the top, the regeneration column has an outlet for the acid gases released. Entrained absorbent vapors can optionally be condensed in a condenser and recycled into the column.

It is possible to connect a plurality of decompression columns in series, in which regeneration is effected at different pressures. For example, regeneration can be effected in a preliminary decompression column at a high pressure typically about 1.5 bar above the partial pressure of the acidic gas constituents in the absorption step, and in a main decompression column at a low pressure, for example 1 to 2 bar absolute. Regeneration with two or more decompression stages is described in publications U.S. Pat. Nos. 4,537,753, 4,553,984, EP 0 159 495, EP 0 202 600, EP 0 190 434 and EP 0 121 109.

The $CO_2$- and $H_2S$-comprising gas stream released in the regeneration step b) can be passed, for example, into a Claus plant. In a Claus plant, the hydrogen sulfide present in the gas stream can be converted to elemental sulfur and permanently removed from the environment. However, even if an $H_2S$-selective absorption and the conversion of hydrogen sulfide to elemental sulfur in a Claus plant are combined, the residual sulfur content in the offgas of the Claus plant (Claus tail gas) is a problem. The residual sulfur contents of the Claus tail gas are generally too high to discharge the Claus tail gas into the environment. The invention therefore also relates to advantageous connections of an $H_2S$-selective absorption and a Claus plant, which include a removal of $H_2S$ from the Claus tail gas and/or an enrichment of $H_2S$ in the feed to the Claus plant.

By means of a downstream hydrogenation plant, the sulfur present in the Claus tail gas or the oxygen-containing sulfur compounds and/or the carbon disulfide can be hydrogenated to hydrogen sulfide. This $H_2S$-containing gas stream can, for example, be purified in turn in a tail gas absorber.

In one embodiment, the above-described process also comprises:
d) a sulfur recovery step in which at least a substream of the $CO_2$- and $H_2S$-containing gas stream released in the regeneration step b) is passed into a Claus plant to obtain a Claus tail gas, and the Claus tail gas is hydrogenated to obtain a hydrogenated Claus tail gas;
e) a second absorption step in which the hydrogenated Claus tail gas is treated with regenerated absorbent to obtain a first $H_2S$-laden absorbent;
f) a step in which the first $H_2S$-laden absorbent is passed into the regeneration step b) and/or into the absorption step a).

The hydrogenated Claus tail gas is passed into a second absorber of which the top stream is $CO_2$-enriched and $H_2S$-depleted. The $CO_2$-enriched and $H_2S$-depleted top stream can be led out of the process, for example sent to an incineration. The bottom stream is a first $H_2S$-laden absorbent, which can be combined with the $CO_2$- and $H_2S$-laden absorbent and passed into regeneration step b). Since the first $H_2S$-laden absorbent is generally not fully laden and can therefore still absorb $CO_2$ and/or $H_2S$, the first $H_2S$-laden absorbent can also be passed fully or partly into the absorption step a) to utilize the residual capacity.

In general, the second absorption step e) is effected at a lower pressure than the absorption step a). Since the $H_2S$ selectivity of the absorbent used in accordance with the invention is higher at relatively low partial $H_2S$ pressures, effective removal of $H_2S$ and enrichment of $H_2S$ in the feed to the Claus plant are achieved in this way.

In a further preferred embodiment, the process also comprises:
d') a third absorption step in which a substream of a $CO_2$- and $H_2S$-containing gas stream released in the regeneration step b) is treated with regenerated absorbent to obtain a second $H_2S$-laden absorbent;
e') a step in which the second $H_2S$-laden absorbent is passed into the regeneration step b).

The embodiment comprises an absorption step in which a substream of the $CO_2$- and $H_2S$-containing gas stream released in the regeneration step b) is treated with regenerated absorbent. The $CO_2$-enriched and $H_2S$-depleted top stream can be led out of the process, for example sent to an incineration. The bottom stream is a second $H_2S$-laden absorbent, which can be combined with the $CO_2$- and $H_2S$-laden absorbent and passed into the regeneration step b). In this way, enrichment of $H_2S$ is achieved in the $CO_2$- and $H_2S$-containing gas stream which is released in the regeneration step b).

In a particularly preferred embodiment of the process, a substream of the $CO_2$- and $H_2S$-laden absorbent from step a) is passed into the third absorption step d'. The remaining absorption capacity of the absorbent from the first absorber can thus be utilized.

In a further preferred embodiment, the above-described process also comprises:
f') a sulfur recovery step in which a substream of the $CO_2$- and $H_2S$-containing gas stream released in regeneration step b) is passed into a Claus plant to obtain a Claus tail gas, and the Claus tail gas is hydrogenated to obtain a hydrogenated Claus tail gas;
g') a second absorption step in which the hydrogenated Claus tail gas is treated with regenerated absorbent to obtain a first $H_2S$-laden absorbent;
h') a step in which the first $H_2S$-laden absorbent is passed into the regeneration step b) and/or into the absorption step a).

The process comprises the treatment of the hydrogenated Claus tail gas in a second absorption step and the treatment of a substream of the $CO_2$- and $H_2S$-containing gas stream released in the regeneration step b) in a third absorption step. In this way, effective enrichment of $H_2S$ is achieved in the feed to the Claus plant.

In a preferred embodiment, which can advantageously be combined with all the embodiments described above, the process also comprises:
i") a recycling step in which a substream of the $CO_2$- and $H_2S$-containing gas stream released in the regeneration step b) is recycled and passed into the absorption step a).

In this way, enrichment of $H_2S$ is achieved in the $CO_2$- and $H_2S$-containing gas stream which is released in the regeneration step b).

In a further preferred embodiment, the $CO_2$- and $H_2S$-laden absorbent is regenerated in two stages, wherein a predominantly $CO_2$-containing gas stream comprising small amounts of $H_2S$ is released in the first stage. The $CO_2$-containing gas stream is subjected to a further absorption step. In this embodiment, the regeneration step b) comprises:

b1) a first regeneration step in which the $CO_2$- and $H_2S$-laden absorbent is decompressed to obtain a $CO_2$-containing gas stream and a partly regenerated absorbent; and
b2) a second regeneration step in which the partly regenerated absorbent is heated and/or stripped to obtain the regenerated absorbent.

The process also comprises:
d") a fourth absorption step in which the $CO_2$-containing gas stream is treated with regenerated absorbent to obtain a third $H_2S$-laden absorbent;
e") a step in which the third $H_2S$-laden absorbent is passed into the regeneration step b).

The removal of a majority of the carbon dioxide from the $CO_2$- and $H_2S$-laden absorbent by decompression enriches the $H_2S$ relative to the $CO_2$ and reduces the plant size and the absorbent circulation.

In a particularly preferred embodiment, the process also comprises:
f') a decompression step in which the $CO_2$- and $H_2S$-laden absorbent is decompressed to a pressure between the pressure in the absorption step a) and the pressure in the first regeneration step b1), in order to release essentially dissolved gas constituents other than carbon dioxide and hydrogen sulfide from the $CO_2$- and $H_2S$-laden absorbent.

This connection variant of the plant allows a higher purity of the $CO_2$-enriched and $H_2S$-enriched gas streams produced.

The invention is illustrated in detail by the appended drawings and the examples which follow. FIGS. 1 to 8 use the same reference symbols for elements of the same function. Plant components not required for understanding, such as pumps, are not shown in the figures for the sake of clarity.

Figure 1:
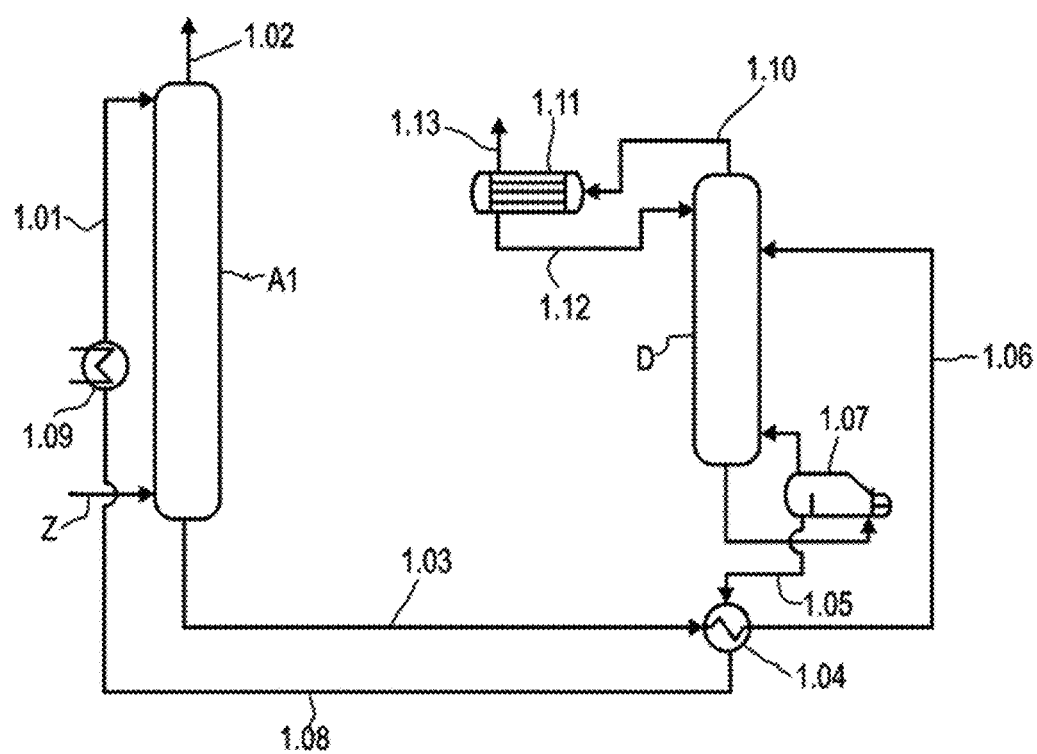
FIG. 1 is a schematic diagram of a plant suitable for performing the process according to the invention.

According to FIG. 1, via the inlet Z, a suitably pretreated gas comprising hydrogen sulfide and carbon dioxide is contacted in countercurrent, in an absorber A1, with regenerated absorbent which is fed in via the absorbent line 1.01. The absorbent removes hydrogen sulfide and carbon dioxide from the gas by absorption; this affords a hydrogen sulfide- and carbon dioxide-depleted clean gas via the offgas line 1.02.

Via the absorbent line 1.03, the heat exchanger 1.04 in which the $CO_2$- and $H_2S$-laden absorbent is heated up with the heat from the regenerated absorbent conducted through the absorbent line 1.05, and the absorbent line 1.06, the $CO_2$- and $H_2S$-laden absorbent is fed to the desorption column D and regenerated.

Between the absorber A1 and heat exchanger 1.04, a flash vessel may be provided (not shown in FIG. 1), in which the $CO_2$- and $H_2S$-laden absorbent is decompressed to, for example, 3 to 15 bar.

From the lower part of the desorption column D, the absorbent is conducted into the boiler 1.07, where it is heated. The mainly water-containing vapor is recycled into the desorption column D, while the regenerated absorbent is fed back to the absorber A1 via the absorbent line 1.05, the heat exchanger 1.04 in which the regenerated absorbent heats up the $CO_2$- and $H_2S$-laden absorbent and at the same time cools down itself, the absorbent line 1.08, the cooler 1.09 and the absorbent line 1.01. Instead of the boiler shown, it is also possible to use other heat exchanger types to raise the stripping vapor, such as a natural circulation evaporator, forced circulation evaporator or forced circulation flash evaporator. In the case of these evaporator types, a mixed-phase stream of regenerated absorbent and stripping vapor is returned to the bottom of the desorption column, where the phase separation between the vapor and the absorbent takes place. The regenerated absorbent to the heat exchanger 1.04 is either drawn off from the circulation stream from the bottom of the desorption column to the evaporator or conducted via a separate line directly from the bottom of the desorption column to the heat exchanger 1.04.

The $CO_2$- and $H_2S$-containing gas released in the desorption column D leaves the desorption column D via the offgas line 1.10. It is conducted into a condenser with integrated phase separation 1.11, where it is separated from entrained absorbent vapor. In this and all the other plants suitable for performance of the process according to the invention, condensation and phase separation may also be present separately from one another. Subsequently, a liquid consisting mainly of water is conducted through the absorbent line 1.12 into the upper region of the desorption column D, and a $CO_2$- and $H_2S$-containing gas is discharged via the gas line 1.13.

Figure 2:
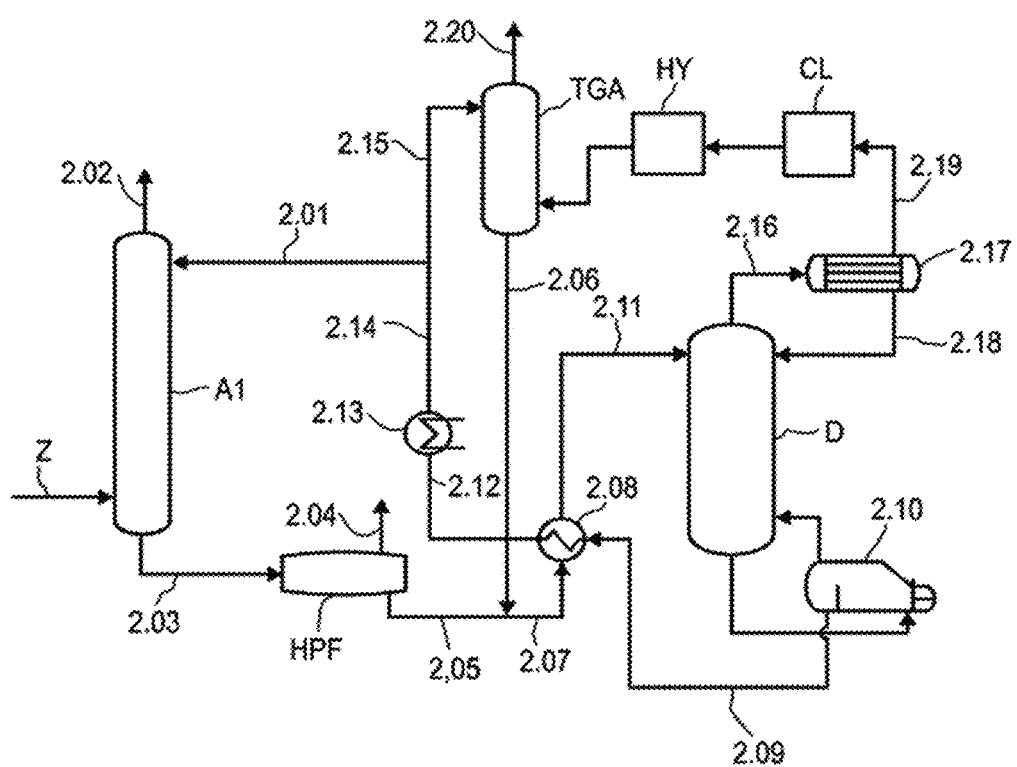
FIG. 2 is a schematic diagram of a further plant suitable for performing the process according to the invention.

According to FIG. 2, via an inlet Z, a suitably pretreated gas comprising $CO_2$ and $H_2S$, preferably natural gas, is contacted in countercurrent, in an absorber A1, with regenerated absorbent which is fed in via the absorbent line 2.01. The absorbent removes $CO_2$ and $H_2S$ by absorption from the gas; at the same time, a $CO_2$- and $H_2S$-depleted gas is obtained via an offgas line 2.02. Via an absorbent line 2.03, the $CO_2$- and $H_2S$-laden absorbent is passed into a decompression vessel HPF and decompressed (for example from about 70 bar to from 3 to 15 bar, preferably 5 to 10 bar), the temperature being essentially equal to the temperature of the laden absorbent. Typically, the temperature differential is less than 10° C., preferably less than 5° C. Under these conditions, essentially all the hydrocarbons present in the laden absorbent are released as gas and can be removed via line 2.04.

Via absorbent line 2.05, 2.07, heat exchanger 2.08 in which the laden absorbent is heated up with the heat from the regenerated absorbent discharged from the lower region of the boiler 2.10 via the absorbent line 2.09, and absorbent line 2.11, the laden absorbent is fed to a desorption column D, where it is regenerated. The regenerated absorbent is conducted into the boiler 4.09, where it is heated. The mainly water-containing vapor is recycled into the desorption column D, while the regenerated absorbent is removed via the absorbent line 2.09, the heat exchanger 2.08, absorbent line 2.12, cooler 2.13 and absorbent line 2.14, and divided into two substreams 2.01 and 2.15 and fed to the absorbers A1 and/or TGA. The relative volume flow rates of streams 2.01 and 2.15 can be varied in order to achieve the desired specifications of the offgas even in the case, for example, of varying $H_2S$ content of the fluid stream to be treated.

The gas which comprises $CO_2$ and $H_2S$ and is obtained in the desorption column D leaves the desorption column D via the gas line 2.16 and is separated from entrained vapor in the condenser with integrated phase separation 2.17, and then a liquid consisting mainly of water is recycled via the absorbent line 2.18 into the upper region of the desorption column D. The gas comprising $CO_2$ and $H_2S$ is fed via the gas line 2.19 to a Claus plant CL, the offgas from which is fed to a hydrogenation plant HY. The hydrogenated Claus tail gas is fed into the tail gas absorber TGA, where it is contacted in countercurrent with the regenerated absorbent fed in via the absorbent line 2.15. Via a gas line 2.20, $CO_2$-enriched gas is removed from the tail gas absorber TGA. Via an absorbent line 2.06, the $H_2S$-laden absorbent is combined with the laden absorbent conducted in line 2.05 and fed via the absorbent line 2.07 to the desorption column D.

Figure 3:
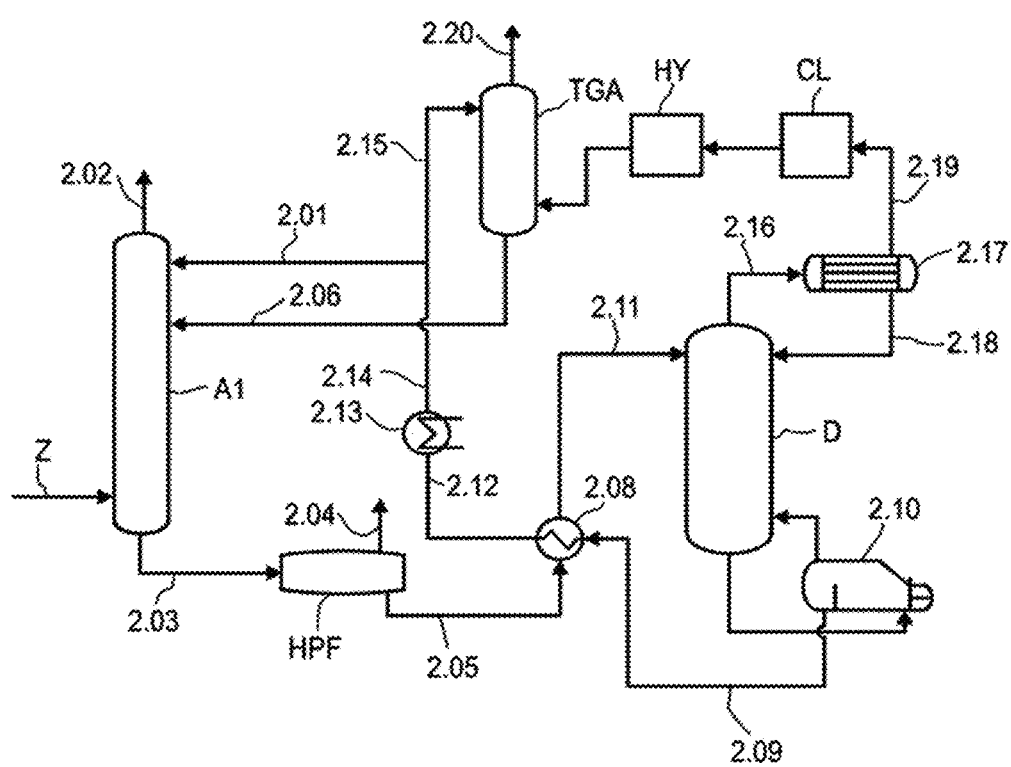
FIG. 3 is a schematic diagram of a further plant suitable for performing the process according to the invention.

The plant shown in schematic form in FIG. 3 corresponds to the plant of FIG. 2, except that the $H_2S$-laden absorbent from the tail gas absorber TGA is fed via the absorbent line 2.06 into the middle region of the absorber A1.

Figure 4:
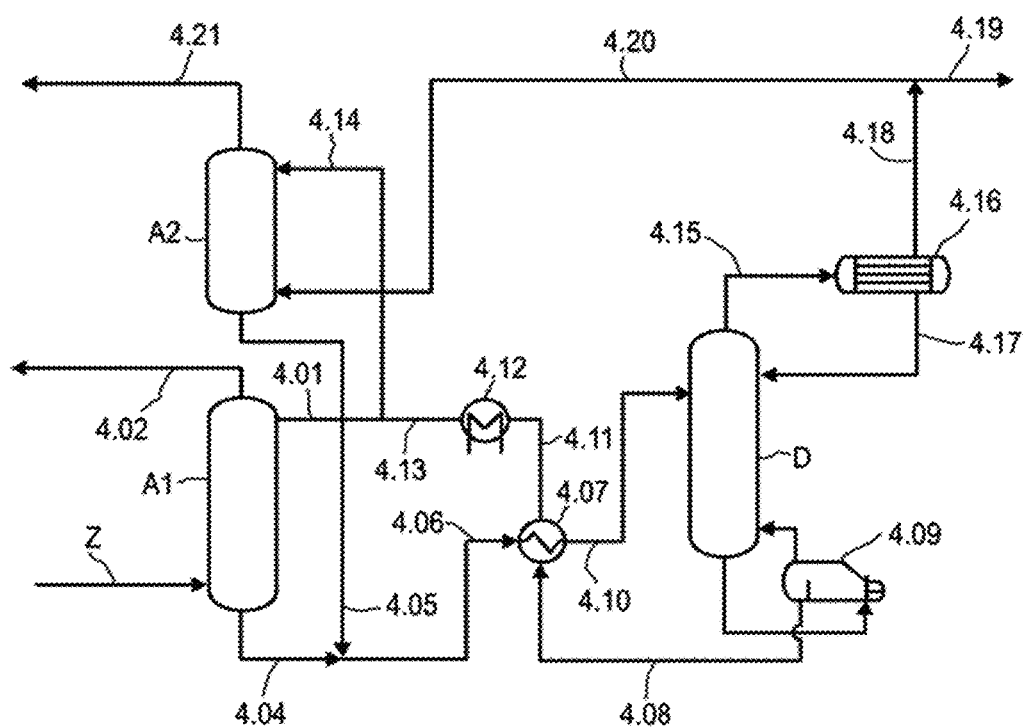
FIG. 4 is a schematic diagram of a further plant suitable for performing the process according to the invention.

According to FIG. 4, via an inlet Z, a suitably pretreated gas comprising $CO_2$ and $H_2S$ is contacted in countercurrent, in an absorber A1, with regenerated absorbent which is fed in via the absorbent line 4.01. The absorbent removes $CO_2$ and $H_2S$ by absorption from the gas; at the same time, a $CO_2$- and $H_2S$-depleted gas is removed via the gas line 4.02.

Via an absorbent line 4.04, absorbent line 4.06, heat exchanger 4.07 in which the $CO_2$- and $H_2S$-laden absorbent is heated up with the heat from the regenerated absorbent discharged from the lower region of the boiler 4.09 via the absorbent line 4.08, and absorbent line 4.10, the $CO_2$- and $H_2S$-laden absorbent is fed to the desorption column D, where it is regenerated. The absorbent is conducted into the boiler 4.09, where it is heated. The mainly water-containing vapor is recycled into the desorption column D, while the regenerated absorbent is removed via the absorbent line 4.08, the heat exchanger 4.07, the absorbent line 4.11, the cooler 4.12 and the absorbent line 4.13. The regenerated absorbent is divided into the substreams 4.01 and 4.14 and fed to the upper region of the absorbers A1 and A2. The relative volume flow rates in the absorbent lines 4.01 and 4.14 can be varied in order to achieve the desired specifications of the offgas even in the case of a varying $H_2S$ content.

The $CO_2$- and $H_2S$-enriched gas obtained in the desorption column D leaves the desorption column D via the gas line 4.15 and is separated from entrained vapor in the condenser with integrated phase separation 4.16, and then a liquid consisting mainly of water is recycled via the absorbent line 4.17 into the upper region of the desorption column D. The $CO_2$- and $H_2S$-enriched gas is removed via the gas line 4.18. A substream is sent to a further treatment via the gas line 4.19, and a substream is fed into the lower region of the absorber A2 via the gas line 4.20.

In the absorber A2, the $CO_2$- and $H_2S$-enriched gas from the line 4.20 is contacted in countercurrent with the regenerated absorbent fed in via the absorber line 4.14. Via a gas line 4.21, the acid gas-depleted absorbent is removed from the absorber A2 and discharged from the plant. Via an absorbent line 4.05, the $H_2S$-laden absorbent from the absorber A2 is combined with the $CO_2$- and $H_2S$-laden absorbent conducted in line 4.04 and fed to the desorption column D via absorbent line 4.06.

Figure 5:
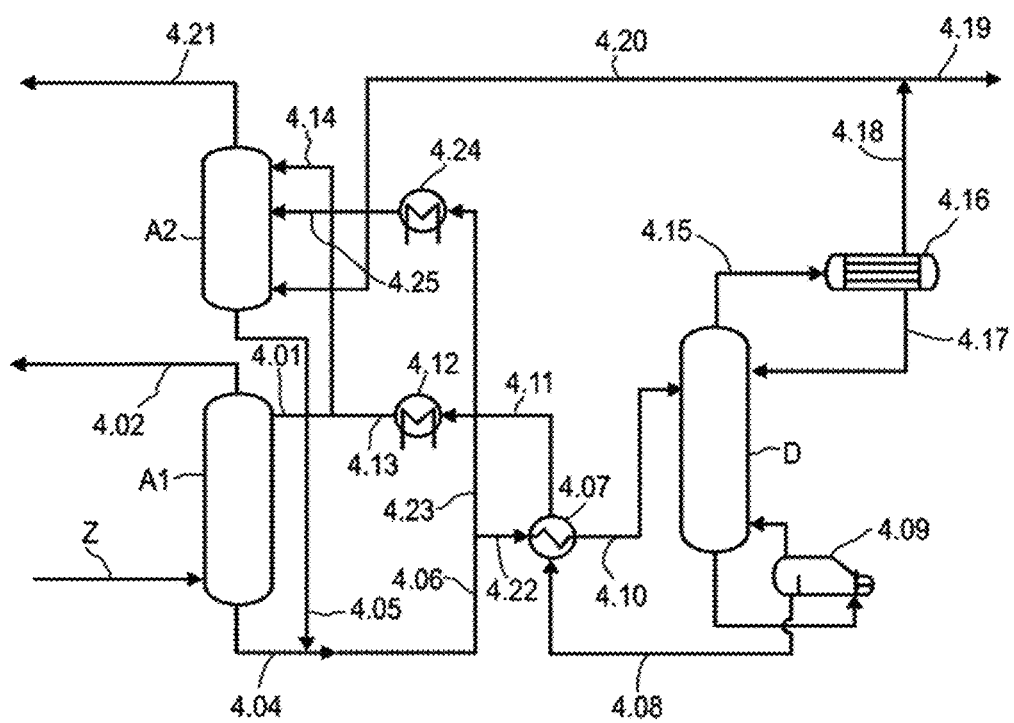
FIG. 5 is a schematic diagram of a further plant suitable for performing the process according to the invention.

The plant shown in schematic form in FIG. 5 corresponds to the plant of FIG. 4, except that a substream of the $CO_2$- and $H_2S$-laden absorbent is passed via the absorbent line 4.23, cooler 4.24 and absorbent line 4.25 into the middle section of the absorber A2.

Figure 6:
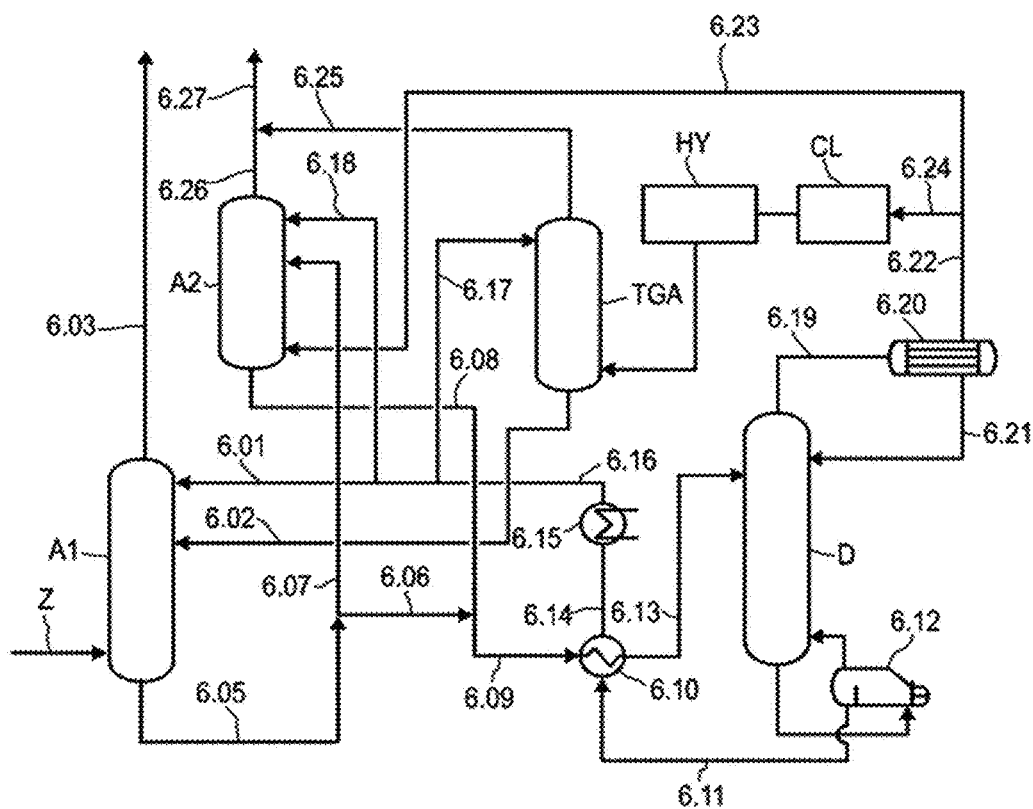
FIG. 6 is a schematic diagram of a further plant suitable for performing the process according to the invention.

According to FIG. 6, via an inlet Z, a suitably pretreated gas comprising $CO_2$ and $H_2S$ is contacted in countercurrent, in an absorber A1, with regenerated absorbent fed in in the upper region via the absorbent line 6.01 and the partly laden absorbent fed in in the middle region via the absorbent line 6.02. The absorbent removes acid gases by absorption out of the gas; this involves removal of an acid gas-depleted gas via the gas line 6.03 and discharge from the plant.

Via absorbent line 6.05, the $CO_2$- and $H_2S$-laden absorbent is drawn off and divided into substreams 6.06 and 6.07. A portion of the laden absorbent is fed via the absorbent line 6.07 into the middle section of the absorber A2. The remaining absorption capacity of the absorbent from absorber A1 can thus be utilized.

The other portion of the $CO_2$- and $H_2S$-laden absorbent is fed via the absorbent line 6.06, absorbent line 6.09, heat exchanger 6.10 in which the $CO_2$- and $H_2S$-laden absorbent is heated up with the heat from the regenerated absorbent discharged from the lower region of the boiler 6.12 via the absorbent line 6.11, and absorbent line 6.13, to a desorption column D, where it is regenerated. The regenerated absorbent is conducted into the boiler 6.12, where it is heated. The mainly water-containing vapor is recycled into the desorption column D, while the regenerated absorbent is conducted onward via the absorbent line 6.11, the heat exchanger 6.10, absorbent line 6.14, cooler 6.15 and absorbent line 6.16, and divided into the substreams 6.01, 6.17 and 6.18. A portion of the regenerated absorbent is conducted via the absorbent line 6.01 into the upper section of the absorber A1, another portion of the regenerated absorbent is conducted via the absorbent line 6.17 into the upper section of the absorber TGA, and a further portion of the regenerated absorbent is conducted via the absorbent line 6.18 into the upper section of the absorber A2. The relative volume flow rates in the absorbent lines 6.01, 6.17 and 6.18 can be varied in order to achieve the desired specifications of the offgas even in the case of a varying $H_2S$ content.

The gas which comprises $CO_2$ and $H_2S$ and is obtained in the desorption column D leaves the desorption column D via the gas line 6.19 and is separated from entrained vapor in the condenser with integrated phase separation 6.20, and then a liquid consisting mainly of water is recycled via the absorbent line 6.21 into the upper region of the desorption column D. The gas comprising $CO_2$ and $H_2S$ is partly fed via the gas line 6.23 into the lower region of the absorber A2.

The other substream of the gas comprising $CO_2$ and $H_2S$ is fed via the gas line 6.24 to a Claus plant CL, the offgas from which is hydrogenated in a hydrogenation plant HY. The hydrogenated Claus tail gas is fed into the tail gas absorber TGA, where it is contacted in countercurrent with the regenerated absorbent fed in via the absorbent line 6.17. Via the absorbent line 6.02, the $H_2S$-laden absorbent from the tail gas absorber TGA is fed into the middle section of the absorber A1. The remaining absorption capacity of the absorbent from tail gas absorber TGA can thus be utilized. Via a gas line 6.25, the $H_2S$-depleted or $CO_2$-enriched gas is removed from the tail gas absorber TGA, combined with the gas stream 6.26 and discharged via gas line 6.27.

In the absorber A2, the gas comprising $CO_2$ and $H_2S$ from gas line 6.23 is contacted in countercurrent with the regenerated absorbent fed in via the absorbent line 6.18 in the upper region and the $CO_2$- and $H_2S$-laden absorbent from absorber A1 fed in via the absorbent line 6.07 in the middle region. Via a gas line 6.26, the acid gas-depleted absorbent is removed from the absorber A2. Via an absorbent line 6.08, an $H_2S$-laden absorbent from the absorber A2 is combined with the laden absorbent conducted in line 6.06 and conducted onward to the desorption column D via absorbent line 6.09.

Figure 7:
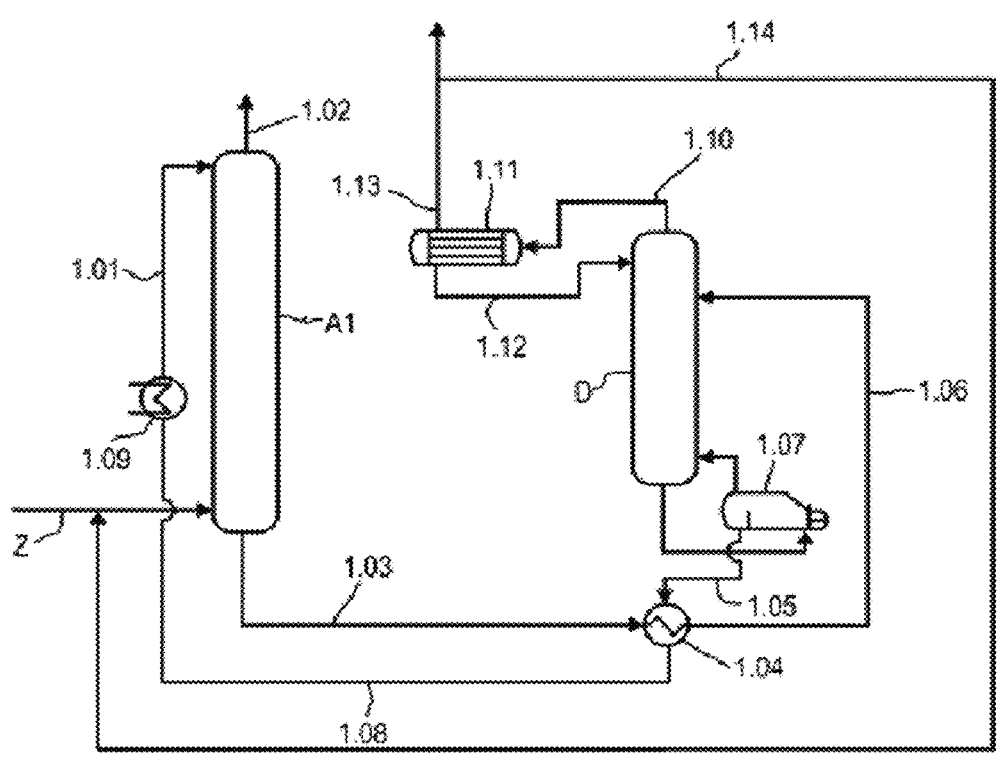
FIG. 7 is a schematic diagram of a further plant suitable for performing the process according to the invention.

The plant shown in schematic form in FIG. 7 corresponds to the plant of FIG. 1, except that a substream of the gas 1.13 comprising $CO_2$ and $H_2S$ is recycled to the inlet Z via the line 1.14. The line 1.14 may comprise a compressor (not shown), which is necessary in plants in which the inlet pressure of the inlet Z is greater than the outlet pressure of the condenser with integrated phase separation 1.11.

Figure 8:
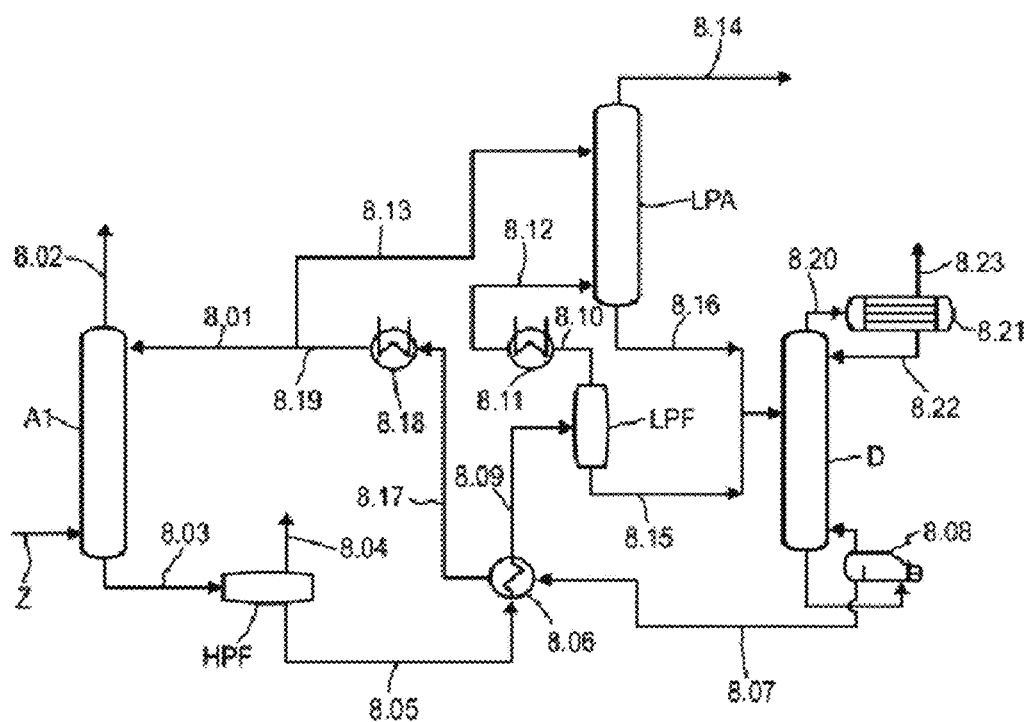
FIG. 8 is a schematic diagram of a further plant suitable for performing the process according to the invention.

According to FIG. 8, via an inlet Z, a suitably pretreated gas comprising $CO_2$ and $H_2S$ is contacted in countercurrent, in an absorber A1, with regenerated absorbent which is fed in via the absorbent line 8.01. The absorbent removes $CO_2$ and $H_2S$ by absorption from the gas; at the same time, a $CO_2$- and $H_2S$-depleted gas is obtained via a gas line 8.02. Via an absorbent line 8.03, the $CO_2$- and $H_2S$-laden absorbent is passed into a decompression vessel HPF and decompressed (for example from about 70 bar to from 3 to 15 bar, preferably 5 to 10 bar), the temperature being essentially equal to the temperature of the laden absorbent. Typically, the temperature differential is less than 10° C., preferably less than 5° C. Under these conditions, essentially all the hydrocarbons present in the laden absorbent are released as gas and can be discharged via line 8.04.

Via an absorbent line 8.05, a heat exchanger 8.06 in which the $CO_2$- and $H_2S$-laden absorbent is heated up with the heat from the regenerated absorbent discharged from the lower region of the boiler 8.08 via the absorbent line 8.07, and an absorbent line 8.09, the laden absorbent is passed into a decompression vessel LPF and decompressed (to less than about 5 bar, preferably less than about 3 bar). Under these conditions, significant portions of the carbon dioxide present in the laden absorbent are released as gas and can be removed via the gas line 8.10 to obtain a partly regenerated absorbent. The $CO_2$ gas here comprises considerable amounts of $H_2S$, which has to be removed before the $CO_2$ can be discharged. For this purpose, the $CO_2$ gas is fed via a cooler 8.11 and the gas line 8.12 into the absorber LPA, where it is contacted in countercurrent with the regenerated absorbent fed in via the absorbent line 8.13. This affords a $CO_2$-enriched gas which is conducted out of the plant via a gas line 8.14.

The partly regenerated absorbent discharged from the lower region of the decompression vessel LPF and the $H_2S$-laden absorbent discharged from the lower region of the absorber LPA is fed via the absorbent lines 8.15 and 8.16 into the upper region of the desorption column D, where it is regenerated. The regenerated absorbent is conducted into the boiler 8.08, where it is heated. The mainly water-containing vapor that results therefrom is recycled into the desorption column D, while the regenerated absorbent is removed via absorbent line 8.07, heat exchanger 8.06, absorbent line 8.17, cooler 8.18 and absorbent line 8.19, and divided into two substreams 8.01 and 8.13 and fed to the absorbers A1 and/or LPA.

The acid gas-enriched gas obtained in the desorption column D leaves the desorption column D via the gas line 8.20 and is fed to the condenser with integrated phase separation 8.21. In the condenser with integrated phase separation 8.21, the gas stream is separated from entrained vapor, and then a liquid consisting mainly of water is conducted via the absorbent line 8.22 into the upper region of the desorption column D, and an acid gas-enriched gas is discharged via the gas line 8.23.

EXAMPLE 1

In a pilot plant, the $H_2S$ selectivity of TBAEE compared to MDEA or TBAEE+MDEA was examined at various absorbent circulation rates.

The pilot plant corresponded to FIG. 1. In the absorber, a structured packing was used. The pressure was 60 bar. The packing height in the absorber was 3.2 m with a column diameter of 0.0531 m. In the desorber, a structured packing was used. The pressure was 1.8 bar. The packing height in the desorber was 6.0 m with a diameter of 0.085 m.

A gas mixture of 96% by volume of $N_2$, 2% by volume of $CO_2$ and 2% by volume of $H_2S$ was conducted into the absorber at a mass flow rate of 47 kg/h and a temperature of 40° C. In the absorber, the absorbent circulation rate was varied from 30 to 100 kg/h. The temperature of the absorbent was 50° C. $H_2S$ was removed to less than 80 ppm. The following table shows the results of these experiments:

| Example | System | Absorbent circulation rate [kg/h] | Selectivity |
|---|---|---|---|
| 1-1* | TBAEE | 30 | —** |
| 1-2 | TBAEE | 42 | 1.14 |
| 1-3 | TBAEE | 60 | 1.11 |
| 1-4* | MDEA | 60 | 1.35 |
| 1-5 | MDEA + TBAEE | 60 | 1.11 |

*comparative examples
**$H_2S$ specification not attained

At the low absorbent circulation rate in comparative example 1-1, the exothermicity of the absorption in the TBAEE-based absorbent was too high, and so it was not possible to achieve a specification of less than 80 ppm of $H_2S$ in the treated fluid stream. At a somewhat higher circulation rate (example 1-2), the separation problem is solved. It is apparent that the selectivity of TBAEE at the same absorbent circulation rate (example 1-3) is lower than that of MDEA (comparative example 1-4). The combination of MDEA+TBAEE (example 1-5) also has a lower selectivity than pure MDEA.

EXAMPLE 2

In an absorption unit according to example 13 of EP 0 084 943 A2, absorption experiments were conducted with various absorbents.

Figure 9:
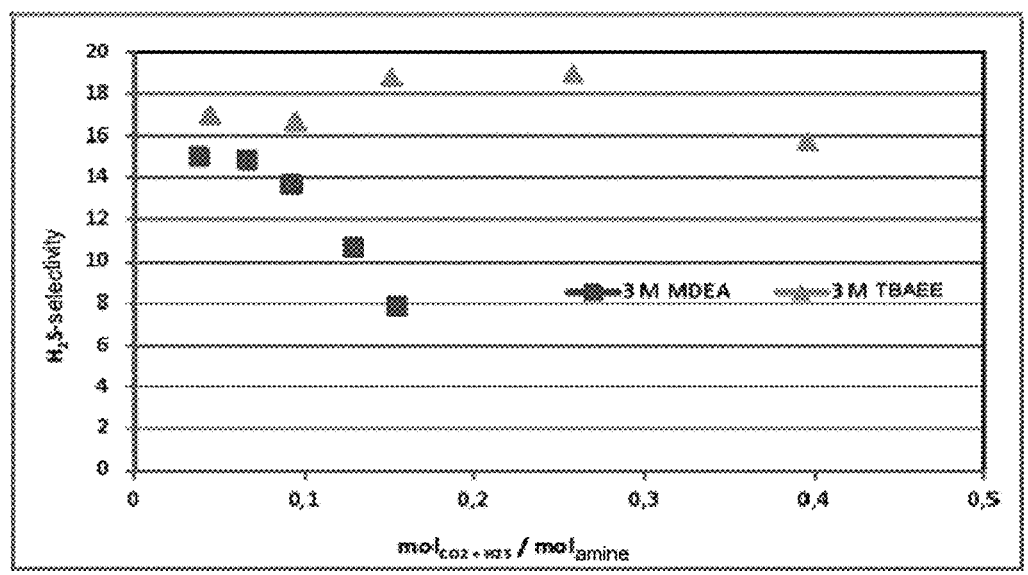
FIG. 9 shows the $H_2S$ selectivity of TBAEE and MDEA as a function of the loading at low partial $H_2S$ pressure.

In a first experiment, a gas mixture of 10% by volume of $CO_2$ (partial $CO_2$ pressure 0.1 bar), 1% by volume of $H_2S$ (partial $H_2S$ pressure 0.01 bar) and 89% by volume of $N_2$ was passed through 100 mL of aqueous absorbent in a glass cylinder at a rate of 216 L (STP)/h and at a temperature of 40° C. The absorbent comprised 3 M MDEA or 3 M TBAEE. Aliquots of the absorbent were drawn off periodically, and the $H_2S$ and $CO_2$ content was determined. The results are shown in FIG. 9. The $H_2S$ selectivity is shown as a function of the loading in mol($CO_2$+$H_2S$) per mole of amine. It is apparent that both MDEA and TBAEE have a high selectivity at low loadings and low partial pressures. With rising loading, the selectivity of MDEA decreases, while TBAEE still has a high $H_2S$ selectivity.

Figure 10:
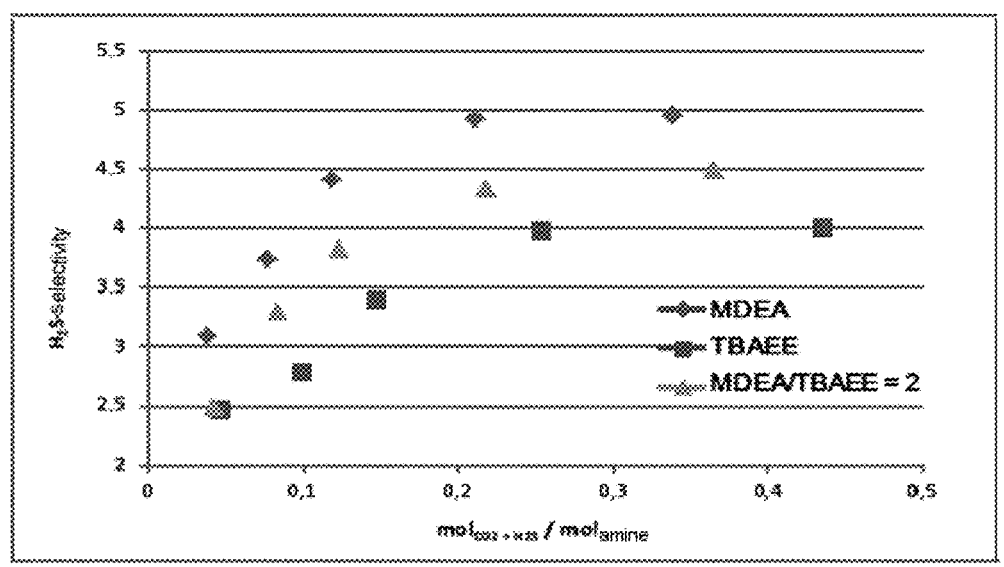
FIG. 10 shows the $H_2S$ selectivity of TBAEE, MDEA and a TBAEE/MDEA mixture as a function of the loading at high partial $H_2S$ pressure.

In a second experiment, a gas mixture of 90% by volume of $CO_2$ (partial $CO_2$ pressure 0.9 bar) and 10% by volume of $H_2S$ (partial $H_2S$ pressure 0.1 bar) was passed through 150 mL of aqueous absorbent in a glass cylinder at a rate of 10 L (STP)/h and at a temperature of 40° C. The absorbent comprised 1.9 M MDEA, 1.9 M TBAEE or 1.4 M MDEA+ 0.5 M TBAEE. Aliquots of the absorbent were drawn off periodically, and the $H_2S$ and $CO_2$ content was determined. The results are shown in FIG. 10. The $H_2S$ selectivity is shown as a function of the loading in mol($CO_2$+$H_2S$) per mole of amine. It was found that, at the greater partial pressures and the higher absorbent circulation rate, the $H_2S$ selectivity rises with increasing loading for all absorbents until a plateau is reached. The $H_2S$ selectivity of MDEA is higher than that of TBAEE, the $H_2S$ selectivity of TBAEE+ MDEA being between MDEA and TBAEE.

EXAMPLE 3

Absorption experiments were conducted in a pilot plant. The pilot plant was constructed as in example 1.

Figure 11:
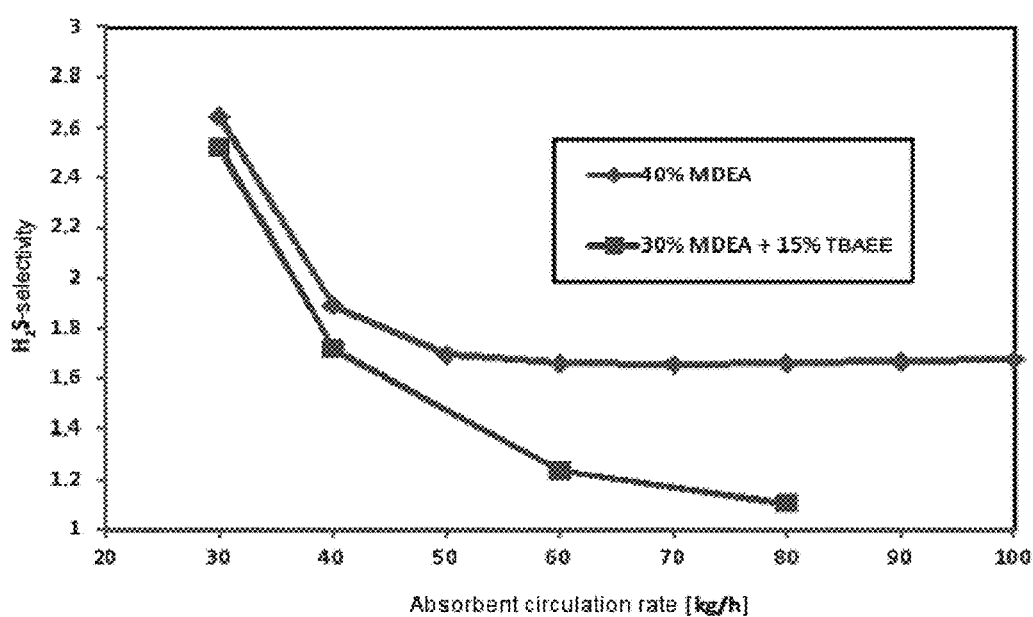
FIG. 11 shows the $H_2S$ selectivity of MDEA and a TBAEE/MDEA mixture as a function of the absorbent circulation rate with constant reboiler output.

The $H_2S$ selectivity of an aqueous absorbent which comprised 40% by weight of MDEA and of an aqueous absorbent which comprised 30% by weight of MDEA and 15% by weight of TBAEE was studied in natural gas at various absorption circulation rates. Concentrations of 5% $CO_2$ and 2% $H_2S$ were present in the natural gas stream. $H_2S$ was removed to less than 10 ppm. The pressure was 60 bar. The energy required to regenerate the absorbent (reboiler output) was kept constant and the resulting $H_2S$ selectivity of the absorbents was examined. FIG. 11 shows the measurement data.

It is apparent that the $H_2S$ selectivity is higher at a low absorbent circulation rate. Here, the selectivities of the absorbents comprising MDEA and MDEA+TBAEE are still close to one another, the selectivity of the MDEA+TBAEE mixture always being lower. In both cases, the selectivity decreases when the absorbent circulation rate is increased. However, from about 50 kg/h upward, the selectivity of the MDEA absorbent is relatively constant, while the selectivity of the MDEA+TBAEE mixture decreases further. Thus, the higher the absorbent circulation rate, the more favorable it is to use TBAEE with MDEA compared to pure MDEA if not only a high level of $H_2S$ removal but also a high carbon dioxide coabsorption is to be achieved while maintaining defined minimum amounts.

EXAMPLE 4

In an absorption unit according to example 13 of EP 0 084 943 A2, absorption experiments were conducted with various absorbents.

Figure 12:
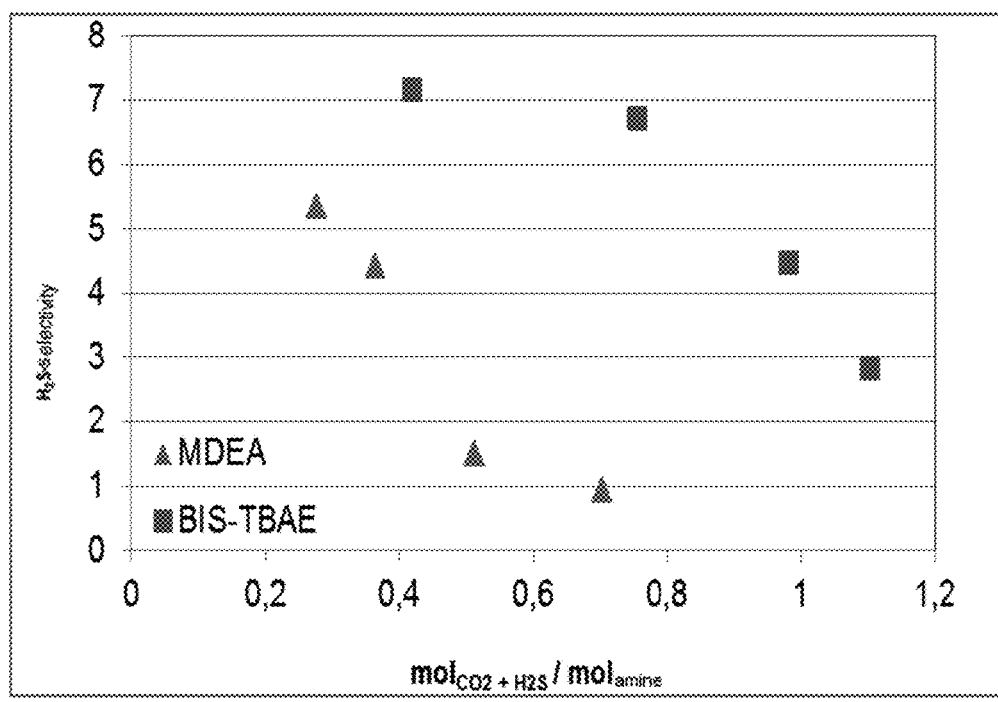
FIG. 12 shows the $H_2S$ selectivity of 1,2-bis(tert-butylamino)ethane (bis-TBAE) and MDEA as a function of the loading at low partial $H_2S$ pressure.

In a first experiment, a gas mixture of 10% by volume of $CO_2$ (partial $CO_2$ pressure 0.1 bar), 1% by volume of $H_2S$ (partial $H_2S$ pressure 0.01 bar) and 89% by volume of $N_2$ was passed through 100 mL of aqueous absorbent in a glass cylinder at a rate of 216 L (STP)/h and at a temperature of 40° C. The absorbent comprised 0.64 M MDEA or 0.64 M 1,2-bis(tert-butylamino)ethane (bis-TBAE). Aliquots of the absorbent were drawn off periodically, and the $H_2S$ and $CO_2$ content was determined. The results are shown in FIG. 12. The $H_2S$ selectivity is shown as a function of the loading in mol($CO_2$+$H_2S$) per mole of amine. It is apparent that, at low loadings and low partial pressures, MDEA and bis-TBAE have relatively similar selectivity. With rising loading, the selectivity of MDEA decreases much more rapidly than the $H_2S$ selectivity of bis-TBAE.

Figure 13:
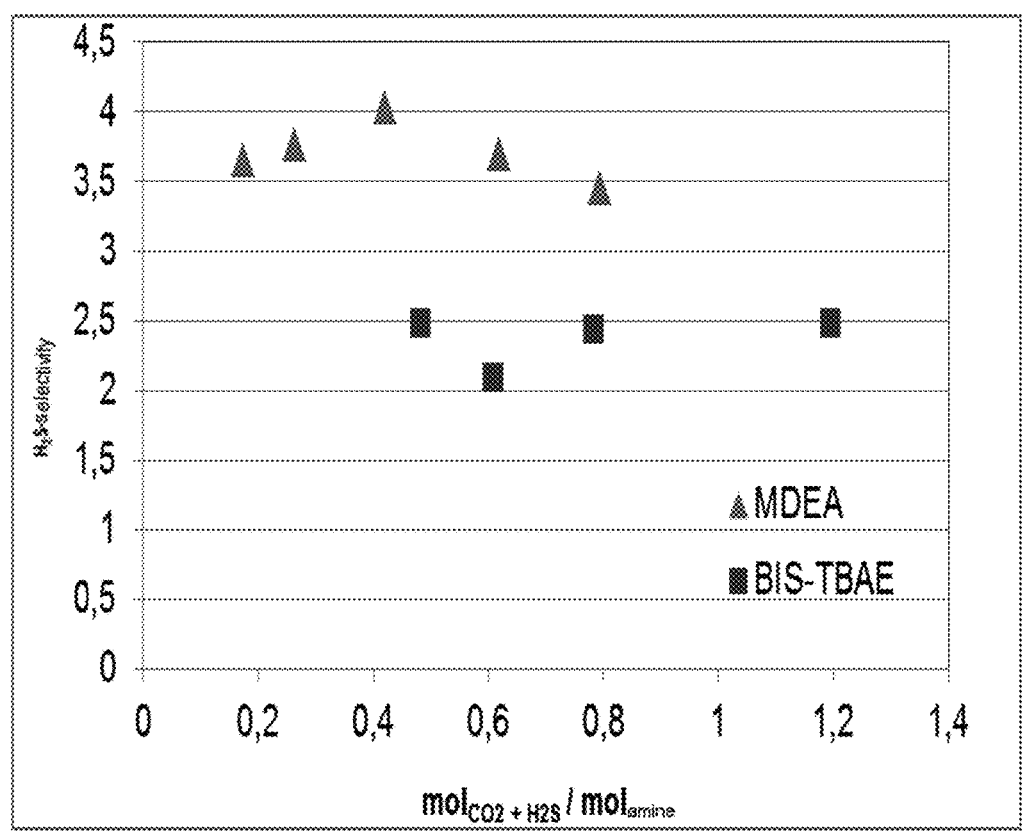
FIG. 13 shows the $H_2S$ selectivity of 1,2-bis(tert-butylamino)ethane (bis-TBAE) and MDEA as a function of the loading at high partial $H_2S$ pressure.

In a second experiment, a gas mixture of 90% by volume of $CO_2$ (partial $CO_2$ pressure 0.9 bar) and 10% by volume of $H_2S$ (partial $H_2S$ pressure 0.1 bar) was passed through 150 mL of aqueous absorbent in a glass cylinder at a rate of 10 L (STP)/h and at a temperature of 40° C. The absorbent comprised 0.64 M MDEA or 0.64 M 1,2-bis(tert-butylamino)ethane (bis-TBAE). Aliquots of the absorbent were drawn off periodically, and the $H_2S$ and $CO_2$ content was determined. The results are shown in FIG. 13. The $H_2S$ selectivity is shown as a function of the loading in mol ($CO_2$+$H_2S$) per mole of amine. It was found that, at the greater partial pressures and the higher absorbent circulation rate, the $H_2S$ selectivity of MDEA is higher than that of bis-TBAE.

The invention claimed is:

1. A process for removing hydrogen sulfide and carbon dioxide from a fluid stream, the process comprising
   a) contacting the fluid stream with an absorbent comprising an aqueous solution of
   (i) an amine of fonnula (I)

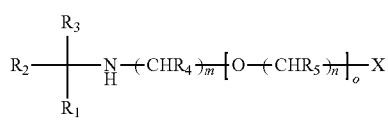

in which $R_1$, $R_2$ and $R_3$ are each independently $C_{1-4}$-alkyl or $C_{1-4}$-hydroxyalkyl; each $R_4$ is independently hydrogen, $C_{1-4}$-alkyl or $C_{1-4}$-hydroxyalkyl; each $R_5$ is independently hydrogen, $C_{1-4}$-alkyl or $C_{1-4}$-hydroxyalkyl; X is OH or $NH(CR_1R_2R_3)$; m is 2, 3, 4 or 5; n is 2, 3, 4 or 5; and o is 0 or 1;
and optionally (ii) at least one tertiary amine, where a molar ratio of (i) to (ii) is greater than 0.05;
wherein there is a partial hydrogen sulfide pressure of at least 0.1 bar and a partial carbon dioxide pressure of at least 1 bar in the fluid stream;
wherein the fluid stream has a total pressure of at least 20 bar;
wherein at least 90% of the hydrogen sulfide is removed from the fluid stream;
wherein a $CO_2$- and $H_2S$-laden absorbent and a treated fluid stream are obtained; and
wherein a selectivity S for hydrogen sulfide over carbon dioxide calculated as follows is not greater than 8:

$$S = \frac{\frac{y(H_2S)_{feed} - y(H_2S)_{treat}}{y(H_2S)_{feed}}}{\frac{y(CO_2)_{feed} - y(CO_2)_{treat}}{y(CO_2)_{feed}}},$$

in which $y(H_2S)_{feed}$ is a molar proportion of $H_2S$ in the fluid stream, $y(H_2S)_{treat}$ is a molar proportion in the treated fluid stream, $y(CO_2)_{feed}$ is a molar proportion of $CO_2$ in the fluid stream and $y(CO_2)_{treat}$ is a molar proportion of $CO_2$ in the treated fluid stream;
   b) regenerating at least a substream of the $CO_2$- and $H_2S$-laden absorbent; to obtain a regenerated absorbent; and
   c) recycling at least a substream of the regenerated absorbent into a)
   d') treating a sub stream of a $CO_2$- and $H_2S$-containing gas stream released in b) with the regenerated absorbent to obtain a second $H_2S$-laden absorbent; and
   e') passing the second $H_2S$-laden absorbent into b).

2. The process according to claim 1, wherein a total concentration of (i) and (ii) in the aqueous solution is 10% to 60% by weight.

3. The process according to claim 1, wherein the amine (i) is 2-(2-tert-butylaminoethoxy)ethanol.

4. The process according to claim 1, wherein the aqueous solution comprises the at least one tertiary amine (ii), which is methyldiethanolamine.

5. The process according to claim 1, wherein the absorbent does not comprise any sterically unhindered primary or secondary amines.

6. The process according to claim 1, wherein the absorbent comprises at least one organic solvent.

7. The process according to claim 1, wherein the fluid stream comprises at least one hydrocarbon.

8. The process according to claim 1, wherein the $CO_2$- and $H_2S$-laden absorbent is regenerated in b) to an $H_2S$ loading corresponding to an equilibrium loading for an $H_2S$ content of less than 90% of a $H_2S$ content of the treated fluid stream.

9. The process according to claim 1, wherein a cumulated $CO_2$ and $H_2S$ loading of the $CO_2$- and $H_2S$-laden absorbent is at least 0.25 mol/mol and a cumulated $CO_2$ and $H_2S$ loading of the regenerated absorbent is less than 0.20 mol/mol.

10. The process according to claim 1, wherein the regenerating b) comprises at least one measure of heating, decompressing and stripping with an inert fluid.

11. The process according to claim 1, wherein a substream of the $CO_2$- and $H_2S$-laden absorbent is passed into d').

12. The process according to claim 1, further comprising i'')recycling and passing into a) a substream of the $CO_2$- and $H_2S$-containing gas stream released in b).

13. The process according to claim 1, further comprising:
   f') passing a substream of the $CO_2$- and $H_2S$-containing gas stream released in b) into a Claus plant to obtain a Claus tail gas, which is hydrogenated to obtain a hydrogenated Claus tail gas;
   g') treating the hydrogenated Claus tail gas with the regenerated absorbent to obtain a first $H_2S$-laden absorbent; and
   h') passing the first $H_2S$-laden absorbent into b) and/or into a).

14. The process according to claim 13, wherein g') is effected at a lower pressure than a pressure in a).

15. The process according to claim 1, wherein b) comprises:
   b1) decompressing the $CO_2$- and $H_2S$-laden absorbent to obtain a $CO_2$-and-$H_2S$-containing gas stream and a partly regenerated absorbent; and
   b2) heating and/or stripping the partly regenerated absorbent to obtain the regenerated absorbent;
   and wherein the process further comprises:
   d") treating the $CO_2$-and-$H_2S$-containing gas stream with the regenerated absorbent of b) to obtain a third $H_2S$-laden absorbent and a $CO_2$-enriched gas stream: and
   e") passing the third $H_2S$-laden absorbent into b).

16. The process according to claim 15, further comprising:
- f") decompressing the $CO_2$- and $H_2S$-laden absorbent to a pressure between a pressure in a) and a pressure in b1), in order to release gas constituents other than carbon dioxide and hydrogen sulfide from the $CO_2$- and $H_2S$-laden absorbent.

* * * * *